(12) United States Patent
Gorden et al.

(10) Patent No.: US 8,052,985 B2
(45) Date of Patent: Nov. 8, 2011

(54) STORAGE-STABLE COMPOSITIONS CONTAINING HYDROGEN CYANAMIDE AND PROPIONIC ACID

(75) Inventors: Anne E. V. Gorden, Auburn, AL (US); Rodrigo Rodriguez-Kabana, Auburn, AL (US)

(73) Assignee: Metbro Distrubuting L.P., Fresno, CA (US)

(*) Notice: Subject to any disclaimer, the term of this patent is extended or adjusted under 35 U.S.C. 154(b) by 572 days.

(21) Appl. No.: 12/253,777

(22) Filed: Oct. 17, 2008

(65) Prior Publication Data

US 2010/0099565 A1  Apr. 22, 2010

(51) Int. Cl.
*A01N 25/02*  (2006.01)

(52) U.S. Cl. ......... 424/405; 424/612; 514/557; 514/609
(58) Field of Classification Search ............... None
See application file for complete search history.

(56) References Cited

U.S. PATENT DOCUMENTS

2010/0099565 A1* 4/2010 Gorden et al. ............ 504/141

* cited by examiner

*Primary Examiner* — Neil Levy
(74) *Attorney, Agent, or Firm* — Kilpatrick Townsend & Stockton LLP.; M. Henry Heines

(57) ABSTRACT

An aqueous storage-stable composition comprises from about 10 to about 35% by weight hydrogen cyanamide, from about 3 to about 25% by weight propionic acid, potassium propionate or ammonium propionate, and water, and has a pH of from about 2.5 to about 4, wherein the concentration of hydrogen cyanamide is greater than the concentration of propionic acid.

9 Claims, 2 Drawing Sheets

STORAGE-STABLE COMPOSITIONS CONTAINING HYDROGEN CYANAMIDE AND PROPIONIC ACID

BACKGROUND OF THE INVENTION

This invention relates to storage-stable aqueous compositions containing hydrogen cyanamide and propionic acid.

As described in U.S. published patent applications 2007/92581 and 2007/116781 of Rodrigo Rodriguez-Kabana, combinations of hydrogen cyanamide and lower alkanoic acids such as propionic acid provide protection of crops against nematode and insect infections, and weed control, by applying such combinations of ingredients to the soil. That patent application describes tests of combinations of varying amounts of hydrogen cyanamide and propionic acid applied at various application rates.

The working examples in US patent applications 2007/92581 and 2007/116781 were carried out by preparing and relatively quickly applying aqueous solutions containing hydrogen cyanamide and a carboxylic acid (usually propionic acid) to soil. Those patent applications also state that the most economical results will generally be achieved when the hydrogen cyanamide concentration is within the range of from about 0.1% to about 10% by weight, preferably from about 0.3% to about 3% by weight and when the concentration of the monocarboxylic acid is within the range of from about 0.1% to about 20% by weight, and preferably from about 1% to about 10% by weight.

When work was carried out to prepare a formulated product comprising combined solutions of hydrogen cyanamide and propionic acid that would be storage stable for lengthy periods of time, it was found that achieving good storage stability required working outside the above proportions of the two ingredients, as well as maintaining pH within a certain range. Otherwise, adverse effects were found to occur, including production of undesirable impurities and/or precipitation of polymers formed in the decomposition of hydrogen cyanamide through reactions to form dimeric imides or propionates.

BRIEF SUMMARY OF THE INVENTION

Accordingly, this invention provides an aqueous storage-stable composition comprising from about 10 to about 35% by weight hydrogen cyanamide, from about 3 to about 25% by weight propionic acid, potassium propionate or ammonium propionate, and water, having a pH of from about 2.5 to about 4, wherein the concentration of hydrogen cyanamide is greater than the concentration of propionic acid.

DETAILED DESCRIPTION OF THE INVENTION

This invention provides an aqueous storage-stable composition comprising from about 10 to about 35% by weight, and preferably from about 25 to about 30% by weight, of hydrogen cyanamide, from about 3 to about 25% by weight, and preferably from about 10 to about 20% by weight, of propionic acid, potassium propionate or ammonium propionate and water, having a pH of from about 2.5 to about 4, preferably from about 3 to about 3.5, wherein the concentration of hydrogen cyanamide is greater than the concentration of propionic acid.

The potassium or ammonium propionate is formed by adding a strong base such as potassium hydroxide or ammonium hydroxide in the preparation of the aqueous composition, in such an amount as to react with some of the propionic acid so as to raise the pH from its incipient value to one of from about 2.5 to about 4, preferably from about 3 to about 3.5, because too low a pH can result in decomposition of the hydrogen cyanamide during storage. On the other hand, raising the pH to a value above about 4 can cause dimerization of the hydrogen cyanamide, forming a diimide.

The amount of propionic acid is chosen so as to provide the necessary combined effects on pests together with the hydrogen cyanamide, as described in US published patent applications 2007/92581 and 2007/116781, as well as to reduce the pH in order to prevent reactions of the hydrogen cyanamide in the aqueous medium. The propionic acid concentration can be as low as 3% by weight if the concentration of hydrogen cyanamide is also low, for example, as low as 10% by weight. If the hydrogen cyanamide concentration is higher, for instance about 25% or more, the propionic acid concentration will be higher as well. Preferably, the hydrogen cyanamide concentration is higher than that of the propionic acid, with the ratio of the two most preferably being about 3:1. In such preferred compositions the hydrogen cyanamide concentration is about 25% and the propionic acid concentration about 8% or 10%, all by weight.

The compositions according to this invention are intended for application to the soil without dilution. A more concentrated preparation, with hydrogen cyanamide content of about 35% by weight, could be produced for subsequent dilution; however, more concentrated solutions can have a reduced shelf life, especially in warmer than room temperatures.

EXAMPLES

The following examples are presented as illustrative of the invention. However, these are only examples, and do not limit the scope of the invention, which is defined only by the claims that follow.

Figure 1:
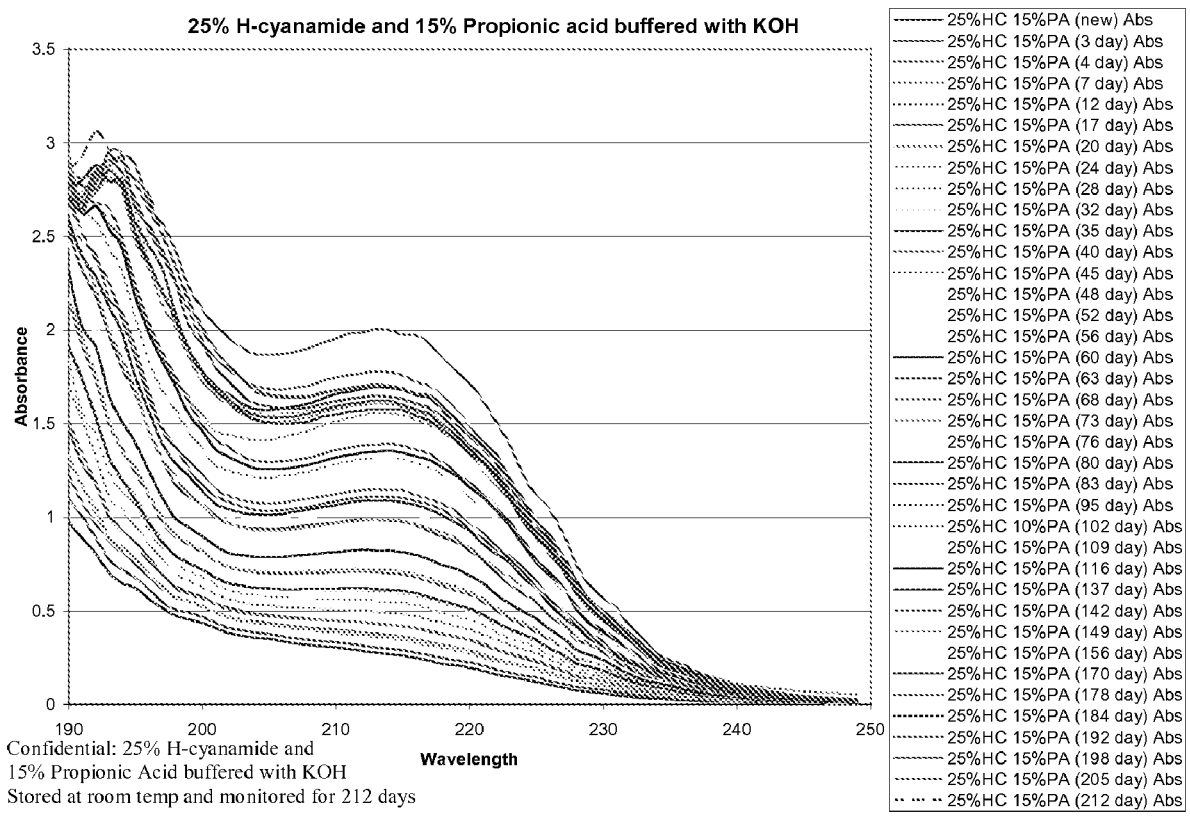
FIG. 1 is the UV absorption spectrum of a composition containing 25 wt. % hydrogen cyanamide and 10 wt. % propionic acid.

Compositions containing hydrogen cyanamide, propionic acid and potassium hydroxide (buffer) were prepared with the concentrations and pH values as described, by mixing the three ingredients with water. The compositions were stored at the indicated temperature for periods of time ranging from 1 to 160 days. Storage stability was assessed periodically after a few days at the indicated temperature, although some tests were continued for a longer period to continue to collect additional data. Test samples were assayed by Ultraviolet-visible (UV-Vis) spectrophotometry to determine whether or not decomposition products had formed. Such products typically had wavelength values of between about 205 and about 220 nm for decomposition products formed by dimerization of hydrogen cyanamide. A test composition was determined to have good storage stability if, after storage for 100 days at 75° F. (room temperature), no more than about 3-5% decomposition products was detected. At higher temperatures, a test composition was determined to have good storage stability after storage for 32 days at 95° F. (35° C.), or for 28 days at 104° F. (40° C.) no more than about 3-5% decomposition products was detected. When stored at reduced temperatures or refrigerated to 10° C., solutions of this invention had extended stability with little to no decomposition detected even after 300 days. FIG. 1 is a representative UV absorption spectrum of various compositions according to the invention. In all cases, the absorption spectrum fell rather quickly after the initial period. An upswing in the curve at a wavelength of about 205-220 indicates the beginning of the formation of decomposition imide products.

Example 1

In this example a composition containing 25 wt. % hydrogen cyanamide and 15 wt. % propionic acid, with sufficient potassium hydroxide to bring the pH up to 3.5, was tested. FIG. 1 is the UV absorption spectrum of that composition. This figure is presented as representative of the spectra of the compositions tested below. The composition was maintained at room temperature for 222 days. The absorbance curve at 205-220 nm began to rise at about 160 days; however, even at 222 days the absorbance had increased only to slightly above 1.5. This formulation thus is considered storage-stable under the above criteria.

Example 2

In this example a composition containing 25 wt. % hydrogen cyanamide and 10 wt. % propionic acid, with sufficient potassium hydroxide to bring the pH up to a value of 3.5, was tested. The composition was maintained at room temperature for 222 days. The absorbance curve at 205-220 nm began to rise at about 124 days; however, even at 222 days the absorbance had increased only to still under 1.5. This formulation thus is considered storage-stable under the above criteria.

Example 3

In this example a composition containing 25 wt. % hydrogen cyanamide and 15 wt. % propionic acid, with sufficient potassium hydroxide to bring the pH up to a value of 3.5, was tested. The composition was maintained at room temperature for 222 days. The absorbance curve at 205-220 nm began to rise at about 109 days; however, even at 212 days the absorbance had increased only to still under 2.0. This formulation thus is considered storage-stable under the above criteria.

Example 4

In this example, a composition containing 25 wt. % hydrogen cyanamide and 20 wt. % propionic acid, with sufficient potassium hydroxide to bring the pH up to a value of 3.5, was tested. The composition was maintained at room temperature for 221 days. The absorbance curve at 205-220 nm began to rise at about 123 days; however, even at 221 days the absorbance had increased only to still well under 2. This formulation thus is considered storage-stable under the above criteria.

Example 5

In this example, a composition containing 25 wt. % hydrogen cyanamide and 25 wt. % propionic acid, with sufficient potassium hydroxide to bring the pH up to a value of 3.5, was tested. The composition was maintained at room temperature for 221 days. The absorbance curve at 205-220 nm began to rise at about 123 days; however, even at 221 days the absorbance had increased only to still well under 2.0. This formulation thus is considered storage-stable under the above criteria.

Example 6

In this example a composition containing 30 wt. % hydrogen cyanamide and 10 wt. % propionic acid, with sufficient potassium hydroxide to bring the pH up to a value of 3.5, was tested. The composition was maintained at room temperature for 222 days. The absorbance curve at 205-220 nm began to rise at about 59 days; however, even at 222 days the absorbance had increased only to still under 2.5. This formulation thus is considered storage-stable under the above criteria.

Figure 2:
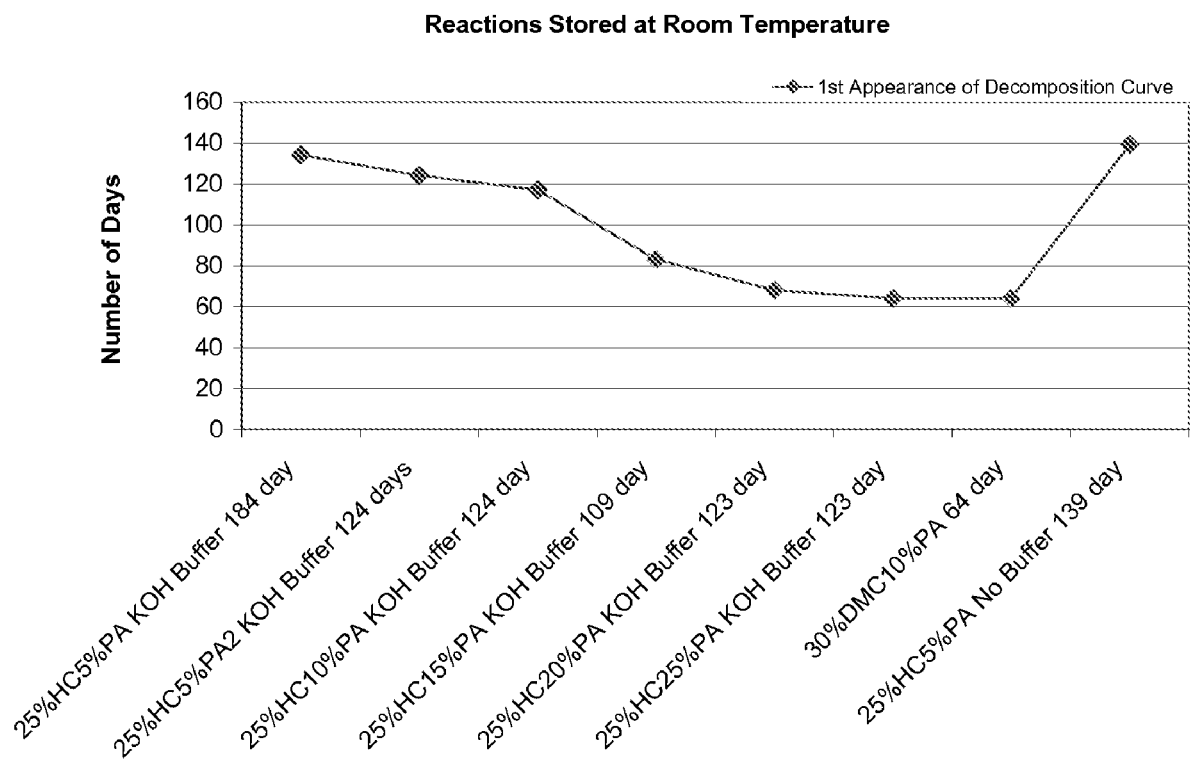
FIG. 2 is a composite taken from data from the examples described below.

FIG. 2 is a composite taken from the data in Examples 1-6, showing the comparable times at which the decomposition first became noticeable on the spectra.

The foregoing descriptions are offered primarily for purposes of illustration. Further modifications, variations and substitutions that still fall within the spirit and scope of the invention will be readily apparent to those skilled in the art. All such modifications coming within the scope of the appended claims are intended to be included therein.

All publications, patents, and patent applications cited herein are hereby incorporated by reference in their entirety for all purposes, except to the extent inconsistent with the disclosure herein.

What is claimed is:

1. An aqueous storage-stable composition comprising from about 10 to about 35% by weight hydrogen cyanamide, from about 3 to about 25% by weight propionic acid, potassium propionate, and water, having a pH of from about 2.5 to about 4, wherein the concentration of hydrogen cyanamide is greater than the concentration of propionic acid.

2. A composition according to claim 1 wherein the weight ratio of hydrogen cyanamide to propionic acid is about 3:1.

3. A composition according to claim 1 wherein the concentration of hydrogen cyanamide is from about 25 to about 30% by weight.

4. A composition according to claim 1 wherein the concentration of propionic acid is from about 10 to about 20% by weight.

5. A composition according to claim 1 wherein the pH is from about 3.0 to about 3.5.

6. A composition according to claim 1 wherein the concentration of hydrogen cyanamide is from about 25 to about 30% by weight, the concentration of propionic acid is from about 10 to about 20% by weight, and the pH is from about 3.0 to about 3.5.

7. A composition according to claim 1 wherein the concentration of hydrogen cyanamide is about 25% by weight, the concentration of propionic acid is about 10% by weight, and the pH is 3.5.

8. A composition according to claim 1 wherein the concentration of hydrogen cyanamide is about 25% by weight, the concentration of propionic acid is about 8% by weight, and the pH is 3.5.

9. A composition according to claim 1 wherein the concentration of hydrogen cyanamide is about 30% by weight, the concentration of propionic acid is about 10% by weight, and the pH is 3.5.

* * * * *